United States Patent
Zahner

(10) Patent No.: US 7,256,034 B2
(45) Date of Patent: Aug. 14, 2007

(54) INHIBITOR OF CELL PROLIFERATION AND METHODS OF USE THEREOF

(75) Inventor: Joseph Edward Zahner, Saint Louis, MO (US)

(73) Assignee: Nucleus Remodeling, Inc., Saint Louis, MO (US)

( * ) Notice: Subject to any disclaimer, the term of this patent is extended or adjusted under 35 U.S.C. 154(b) by 185 days.

(21) Appl. No.: 10/751,380

(22) Filed: Jan. 5, 2004

(65) Prior Publication Data

US 2004/0138419 A1 Jul. 15, 2004

Related U.S. Application Data

(63) Continuation of application No. 10/083,889, filed on Feb. 27, 2002, now Pat. No. 6,673,894.

(60) Provisional application No. 60/271,798, filed on Feb. 27, 2001.

(51) Int. Cl.
*C12N 1/00* (2006.01)
*C12N 1/15* (2006.01)
*C12N 15/00* (2006.01)
*C12N 5/00* (2006.01)
*C07H 21/04* (2006.01)

(52) U.S. Cl. .......................... 435/254.11; 435/254.23; 435/320.1; 435/325; 435/419; 536/23.4

(58) Field of Classification Search ............ None
See application file for complete search history.

*Primary Examiner*—Nancy Vogel
*Assistant Examiner*—Walter Schlapkohl
(74) *Attorney, Agent, or Firm*—Joseph E. Zahner

(57) ABSTRACT

An chimerical polypeptide that arrests proliferating cells in mitosis is provided. In general the polypeptide has an N-terminal transit peptide, such as HIV-1 Tat, and a C-terminal cell-cycle effector, such as a G2/M cyclin or a cytostatic factor. A polynucleotide under the control of a heterologous promoter that encodes a polypeptide that arrests cells in mitosis is also provided. The polynucleotide may, for example, encode a G2/M cyclin. Pharmaceutical compositions comprising the agent that inhibits transit through mitosis is provided. A method of treating patients suffering from a hyperplasia, such as cancer, psoriasis or benign prostate hyperplasia is provided.

6 Claims, 2 Drawing Sheets

Tat-cyclin B PCR Product pGAPZaA-Tat-cyclin B Plasmid

INHIBITOR OF CELL PROLIFERATION AND METHODS OF USE THEREOF

This application is a continuation of U.S. patent application Ser. No. 10/083,889, filed Feb. 27, 2002, which issued as U.S. Pat. No. 6,673,894 on Jan. 6, 2004 and which claims the benefit of priority to U.S. Provisional Patent Application No. 60/271,798, filed Feb. 27, 2001, which is now abandoned.

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION (1) Field of the Invention

This invention relates generally to recombinant polypeptides, and polynucleotides encoding those peptides, that arrest proliferating cells in mitosis, and to methods of treating patients with hyperplasias by administering pharmaceutical compositions comprising recombinant polypeptides or polynucleotides.

(2) Description of the Related Art

Cell proliferation in normal cells is regulated by growth factors that signal the cell to re-enter the cell cycle from a state of quiescence. For example, when wounding occurs, growth factors, e.g., platelet-derived growth factor, stimulate fibroblasts to proliferate. Under normal circumstances, withdrawal of growth factors causes proliferating cells to exit the cell cycle and become quiescent. Cancer cells (neoplasia) have lost the ability to exit the cell cycle and proliferate in the absence of growth factors. That is, the cancer cells think that they are receiving growth factor signals. On the other hand, most benign hyperplasias result from the hyperproliferation of cells due to the inappropriate or uncontrolled secretion of growth factors.

Transition across the G2-M border is crucial to advancement through the cell cycle. The G2-M transition is controlled by the activation of the cyclin-dependent kinase cdc2 by the cyclin B. For a review on the regulation of the cell cycle by the cyclin B/cdc2 complex, see Bastians et al., 1999). Basically, levels of cyclin B accumulate during interphase until they reach an optimal level near the end of G2, at which time, cyclin B binds to and activates the kinase cdc2. The active cyclin B/cdc2 complex phosphorylates various molecules that facilitate the entry into mitosis. The level of cyclin B/cdc2 within the nuclei of proliferating cells reach a maximum at metaphase, upon which time cdc2 activates the destruction of cyclin B. Upon the destruction of cyclin B, the cells are then able to undergo anaphase and hence complete the cell cycle.

Diseases of uncontrolled cell proliferation, or hyperplasias, are common health problems today. Examples of diseases of cell over-proliferation include psoriasis, seborrhea, eczema, benign prostate hyperplasia, congenital adrenal hyperplasia, endometrial hyperplasia, squamous cell (vulvular) hyperplasia, sebaceous hyperplasia, Crohn's Disease, leukemia, carcinoma, sarcoma, glioma, and lymphoma. Current treatment protocols for these diseases are generally toxic and/or ineffective as permanent cures.

Current cancer therapies involve the use of mitotic poisons, such as taxol or colcemid, or radiation to induce cell death in rapidly dividing cells. Such an approach attempts to kill cancer cells at a faster rate than healthy, naturally proliferating cells. Current forms of chemotherapy have severe side affects due to the destruction of healthy tissue, and are therefore a compromise at best.

Current treatments for other hyperplasias, such as benign enlarged prostate or psoriasis and eczema, are largely based upon the use of steroids or retinoids. For example, psoriasis is commonly treated by oral administration of drugs that engage receptors for glucocorticoids, retinoids and vitamin D, i.e., lipid soluble hormones which bind to nuclear receptors. Much of the current research in psoriasis treatment is now focused on the thiazolidinedione class of drugs that bind to the newly discovered peroxisome proliferator-activated receptor gamma. These drugs are administered orally and target multiple cellular processes, therefore leading to potential side effects. For a review on oral steroid-like treatments for psoriasis, see Pershadsingh, HA, 1999 and Ellis, et al., 2000.

Routine topical treatments for psoriasis and/ or eczema include steroid creams that are applied to the skin. However, the use of steroids is associated with several side effects including skin thinning, stretch marks and discoloration. Recently, a new cream called PROTOPIC®, which comprises an immunomodulatory drug called tacrolimus (Asakura, et al., 1999, U.S. Pat. No. 5,955,469), has been approved as a topical therapy for eczema. Although the use of a topical immunomodulator may have advantages over the use of steroidal based creams, immunomodulators exert their effects on the immune system. For individuals who are immunocompromised, the use of steroidal creams or creams containing immunosuppressing immunomodulators could possibly have deleterious effects.

Phototherapy, in the form of UVA or UVB irradiation, either used alone, or in combination with other forms of therapy, is a common treatment for inflammatory skin diseases. An important drawback to using ultraviolet light is the heightened risk of skin cancer in the recipient of such treatment. For a review of recent advances in phototherapy, see Simon, et al., 2000.

Many dermatological diseases such as, for example, psoriasis, eczema and seborrhoea, have two major components, inflammation and hyperproliferation. The current standard treatments for these diseases primarily target the inflammation aspect of the diseases.

There have been some efforts in the development of treatments targeting hyperproliferation of cells. Sato et al, have recently reported that the overexpression of platelet-activating factor receptor (PAFR) in transgenic mice leads to epidermal hyperproliferation that resembles psoriasis. Topical application of a cream comprising the PAFR antagonist WEB2086 to the transgenic mice resulted in the suppression of the number of proliferating cells (Sato, et al., 1999)

Benign prostate hyperplasia (BPH), or enlarged prostate, is another economically important disease of cell hyperproliferation. Over 30% of men in their 70s suffer from BPH and, while the growth in and of itself is harmless, it can lead to other serious urogenital disorders. For example, BPH causes problems in urination and can lead to serious kidney disorders, incontinence and impotence. Over 400,000 prostatectomies are performed each year in the United States. Even though surgical prostatectomy can cause bleeding, infection, impotence, retrograde ejaculation and incontinence, it still remains the predominant therapy for BPH.

In addition to the traditional surgical resection procedures, which are used to open the constricted urethral lumen or to remove the entire prostate, several new surgical methods are being developed for BPH. These novel surgical treatments include microwave thermotherapy, transurethral electrovaporization, laser ablation (Bolmsjo et al., 2000, Ohtani et al., 1999, Gilling et al., 1996). Although these treatments are effective toward correcting bladder retention symptoms, they are surgical and as such may increase the chances of secondary complications such as incontinence and impotence.

Other medical treatments for BPH include the administration of finastride (a 5-alpha reductase inhibitor) or alpha-adrenoceptor antagonists (alpha blockers). Finastride is a 4-aza steroid compound that inhibits the conversion of testosterone to dihydrotestosterone (Stoner, 1990). In clinical trials, finastride has been shown to increase urine flow rate by 30% and to decrease prostate size by 18%. However, users of finastride complain of impotence and decreasing libido, suggesting that this drug affects other physiological pathways (Carraro et al., 1996).

Other agents used to treat BPH are alpha blockers. Alpha-blockers are alpa-adrenergic receptor antagonists, which act by relaxing the smooth muscle cells of the prostate, thereby facilitating the flow of urine through the urethra. Additionally, other classes of alpha blockers have been shown to actually suppress prostate growth by inducing apoptosis of prostate epithelial cells. These novel pro-apoptotic effects of some alpha blockers are independent of the alpha-adrenoceptor antagonism (Kyprianou et al., 2000). Side effects of alpha blocker treatment include dizziness, headache, drowsiness and retrograde ejaculation.

The development of safe and effective drugs with specific cell proliferation inhibiting properties would bring significant improvements in the treatment of hyperplasia and cancer. Such drugs can be used alone or in conjunction with current conventional treatments for cancer or hyperplasias, to improve the safety and efficacy of those treatments. This invention is directed to polypeptide and polynucleotide based cell cycle effectors that specifically and narrowly block only the G2/M transition of actively proliferating cells, and the use thereof. By specifically affecting only those cells that have committed to undergo mitosis, the invention would be expected to have little to none side effects. Thus,the development and commercialization of new treatments that safely and effectively target the cellular hyperproliferation aspect of cancer and/or hyperplasia diseases is sorely needed.

(3) References and Related Art (i) Patent Documents

Asakura et al., Sep. 21, 1999, U.S. Pat. No. 5,955,469. "Pharmaceutical composition."
Beach et al., Dec. 9, 1997, U.S. Pat. No. 5,695,950. "Method of screening for antimitotic compounds using the cdc25 tyrosine phosphatase."
Beach et al., Oct. 5, 1999, U.S. Pat. No. 5,962,316. "Cell-cycle regulatory proteins, and uses related thereto."
Beach et al., Oct. 19, 1999, U.S. Pat. No. 5,968,821. "Cell-cycle regulatory proteins, and uses related thereto."
Beach et al., Mar. 28, 2000, U.S. Pat. No. 6,043,030. "Cell-cycle regulatory proteins, and uses related thereto."
Giordano, Dec. 19, 2000, U.S. Pat. No. 6,162,612. "Human cyclin-dependent kinase-like proteins and methods of using the same."
Henderson et al., Dec. 16, 1997, U.S. Pat. No. 5,698,443. "Tissue specific viral vectors."
Kauffman et al., May 24, 1994, U.S. Pat. No. 5,314,688. "Local delivery of dipyridamole for the treatment of proliferative diseases
Wu et al., Jun. 3, 1997, U.S. Pat. No. 5,635,383. "Method for the introduction of genes into mammalian cells by a soluble molecular complex comprising a receptor ligand and a polycation."
Weiner et al., Jan. 9, 2001, U.S. Pat. No. 6,172,201. "Cellular receptor for HIV-1 Vpr essential for G2/M phase."

(ii) Other References

Bolmsjo et al., 2000, "Cell-kill mdeoling of microwave thermotherapy for treatment of benign prostatic hyperplasia." *J. Endourol* 14:627–635.
Carraro et al., 1996, "Comparison of phytotherapy (Permixon) with finestride in the treatment of benign prostate hyperplasia: a randomized international study of 1,098 patients." *Prostate* 29:231–242.
Bastians et al., 1999, "Cell cycle-regulated proteolysis of mitotic target proteins." *Mol. Biol. Cell* 10:3927–3941.
Djavan, B. and M. Marberger, 2000, "Transurethral microwave thermotherapy: an alternative to medical management in patients with benign prostatic hyperplasia." *J. Endourol.* 14:661–669.
Ellis et al., 2000, "Troglitazone improves psoriasis and normalizes models of proliferative skin disease: ligands for peroxisome proliferator-activated receptor-gamma inhibit keratinocyte proliferation." *Arch Dermatol* 136: 609–616.
Foldvari, et al., 1999, "Dermal and transdermal delivery of protein pharmaceuticals: lipid-based delivery systems for interferon α." *Biotechnol. Appl. Biochem.* 30:129–137.
Gariepy, J. and K. Kawamura, 2001, "Vectorial delivery of macromolecules into cells using peptide-based vehicles." *Trends Biotech.* 19:21–28.
Gilbert, S., 1997, *Developmental Biology*, 5th ed., pp. 200–201, Sinauer, Sunderland, Mass.
Gilling, et al., 1996, "The use of the holmium laser in the treatment of benign prostatic hyperplasia." *J. Endourol.* 10:459–461.
King, R., et al., 1996, "Mutagenic analysis of the destruction signal of mitotic cyclins and structural characterization of ubiquitinated intermediates." *Mol. Biol. Cell* 7:1343–1357.
Kyprianou et al., 2000, "Effects of Alpha(1)-adrenoceptor (alpha(1)-AR) antagonists on cell proliferation and apoptosis in the prostate: therapeutic implications in prostatic disease." *Prostate Suppl.* 9:42–46.
Ohtani, et al., 1999, "A new parameter in decision making for transurethral electroresection of benign prostate hyperplasia." *Eur. Urol.* 35:185–191.
Pershadsingh, H A, 1999, "Pharmacological peroxisome proliferator-activated receptor gamma ligands: emerging clinical indications beyond diabetes." *Expert Opin Investig Drugs* 8:1859–1872.
"Pichia expression vectors for constitutive expression and purification of recombinant proteins", Version C, Invitrogen Corporation, Carlsbad, Calif., 2000.
Sato et al., 1999, "Accelerated proliferation of epidermal keratinocytes by the transgenic expression of the platelet-activating factor receptor." *Arch Dermatol.* 291:614–621.
Sebok, et al., 2000, "Tazarotene induces epidermal cell differentiation in the mouse tail test used as an animal model for psoriasis." *Skin Pharmacol. Appl. Sin Physiol.* 13:285–291.
Simon et al., 2000, "Recent advances in phototherapy." *Eur J Dermatol* 10:642–645.
Stoner, E., 1990, "The clinical development of a 5 alpha-reductase inhibitor, finestride." *J. Steroid Biochem. Mol. Biol.* 37:375–378.
Vorlaufer and Peters, 1998, "Regulation of the Cyclin B degradation system by an inhibitor of mitotic proteolysis." *Mol. Biol. Cell* 9:1817–1831.
Yamano, H., et al., 1998, "The role of the destruction box and its neighboring lysine residues in cyclin B for anaphase ubiquitin-dependent proteolysis in fission yeast: defining the D-box receptor." *EMBO J.* 17:5670–5678.

SUMMARY OF THE INVENTION

Improved treatments targeted toward hyper-proliferative diseases would take advantage of the fact that the disease cells remain in the cell cycle, and therefore target the molecular processes that directly control the cell cycle. The present invention describes a novel, useful and safe composition which is used in the treatment of diseases of cell over-proliferation.

The present invention is based upon the unexpected discovery that a chimeric polypeptide, which is comprised of an N-terminal Tat transit peptide and a C-terminal cyclin B peptide, when added to the liquid media of proliferating HeLa cells, causes the HeLa cells to stop dividing indefinitely (see Example 3). Furthermore, the cells remained healthy in appearance.

One embodiment of the present invention is directed toward polypeptides that arrest eukaryotic cell proliferation. The polypeptide comprises at least a transit peptide domain and an effector domain. The transit peptide domain allows the entire polypeptide to cross the plasma membrane of cells. Transit peptides are well known in the art (Gariepy and Kawamura, 2001).

The effector domain functions to arrest eukaryotic cells in mitosis. In one embodiment of the chimeric polypeptide, the effector domain comprises a portion of a cyclin B or any G2/M cyclin derived from any eukaryotic organism. The cyclin B or any G2/M cyclin may contain amino acid deletions, insertions or substitutions which block the degradation of the polypeptide by the ubiquitin-proteosome complex. In another embodiment of the chimeric polypeptide, the effector domain comprises a portion of a c-Mos polypeptide or any polypeptide that prevents the degradation of a cyclin.

In another embodiment, the invention is directed to an isolated and purified polynucleotide encoding a product which functions to arrest a eukaryotic cell in mitosis. In a prefered embodiment of the polynucleotide, the polynucleotide encodes a portion of a cyclin B, or any G2/M cyclin, under the control of a constitutive or regulatable promoter. The coding region of the cyclin may contain mutations which stabilize or block the degradation of the cyclin mRNA or polypeptide. In another embodiment of the polynucleotide, the polynucleotide encodes a portion of a cMos polypeptide, or any polypeptide which blocks the degradation of a cyclin, under the control of a constitutive or regulatable promoter.

In another embodiment, the invention is directed to a pharmaceutical composition comprising a chimeric polypeptide which arrests eukaryotic cell proliferation. An alternative embodiment of a pharmaceutical composition comprises a polynucleotide encoding a polypeptide which arrests eukaryotic cell proliferation under the control of a constitutive or regulatable promoter.

In another embodiment, the invention is directed to methods of reducing cell proliferation in a patient who suffers from a hyperplasia. The method comprises treating the patient with a pharmaceutical composition comprising a chimeric polypeptide or a recombinant polynucleotide encoding a polypeptide which blocks cell proliferation. In a prefered embodiment, the treatment is directed to patients who suffer from dermal or epidermal hyperplasias such as, for example, psoriasis, eczema, seborrhea, and/or other dermatites. In another embodiment, the treatment is directed to patients that suffer from benign prostate hyperplasia. In another embodiment, the treatment is directed to patients that suffer from cancer, wherein said cancer may be a carcinoma, lymphoma, sarcoma, glioma, myeloma, or leukemia.

DETAILED DESCRIPTION OF THE INVENTION

Figure 1:
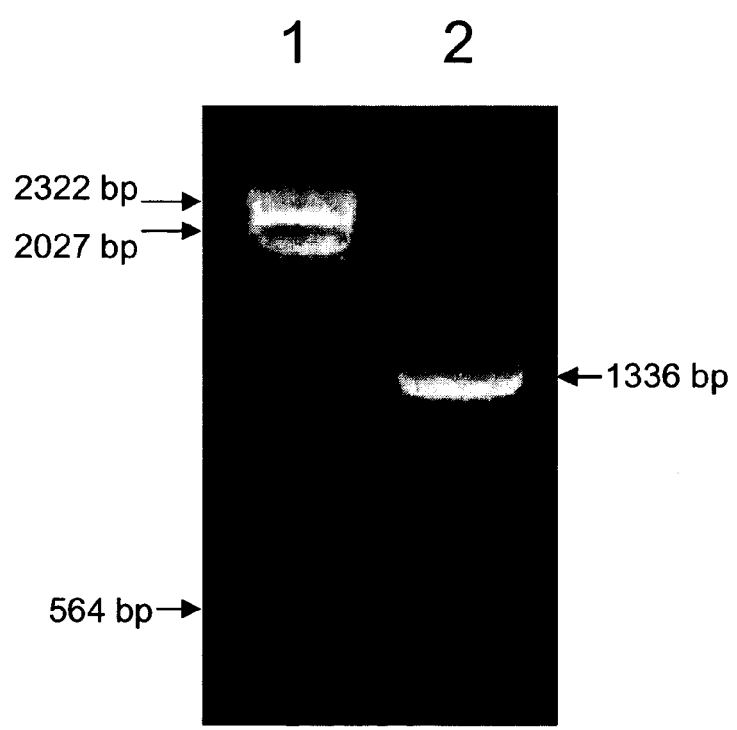
FIG. 1 depicts an ethidium bromide stained agarose gel depicting a DNA fragment encoding Tat-cyclin B of SEQ ID NO:25, produced by the polymerase chain reaction.

The present invention pertains to compositions and methods directed toward treating hyperplasias or neoplasias through the maintenance of levels of cyclin B within cells, such that the proliferating cells are unable to transit past metaphase to complete mitosis. It has been discovered rather unexpectedly that exogenously applied cyclin B covalently linked to a transit peptide virtually arrests HeLa cell proliferation. Example 3 describes this experiment and the results are presented in Table 4.

As mentioned above, cyclin B is necessary for the progression of cells through the cell cycle and that the prevention of cyclin B accumulation in the cell could result in the inhibition of cell proliferation. For the purposes of understanding the present invention, it is important to note that cells can only get past metaphase upon the destruction of cyclin B by the proteosome. The preferred embodiments of the invention are specifically directed toward maintaining high intranuclear levels of G2/M cyclins.

Several prior art documents disclose methods of interfering with the G2/M transition. Vorlaufer and Peters (1998), teach drugs that block ubiquitin-mediated proteolysis. However such drugs indescriminantly affect other ubiquitin/proteosome functions and are therefore expected to have adverse side effects. Weiner et al (U.S. Pat. No. 6,172,201) teach an HIV derived peptide called Vpr, which may block the G2/M transition. However, Vpr has several other activities, which are undesirable in a treatment for hyperplasia, including importing of reverse transcriptase into the nucleus of non-dividing cells, cellular differentiation and enhancement of HIV-1 replication. The invention is directed to isolated and purified recombinant polypeptides, recombinant polynucleotides, pharmaceutical compositions and treatments for diseases which involve hyperplasia.

The first embodiment of the invention is directed to an isolated and purified polypeptide which can freely cross the eukaryotic cell membrane, enter the nucleus and block the progression of said cell through mitosis. The affect of such a polypeptide is to arrest the proliferation of cells which are committed to divide. The essential qualities of the polypeptide are 1) that the polypeptide block progression of the cell through the cell cycle, 2) that the polypeptide be able to move freely across the cell membrane and subsequently into the nucleus, and 3) that the polypeptide not be toxic to surrounding cells or tissue.

It is well known in the art that cyclins control the step wise transition of cells through the cell cycle by regulating the activity of cyclin dependent kinases, which in turn go on to effect essential processes within the cells. For cells to progress from G2 through mitosis, G2/M-type cyclins, of which cyclin B is an example, are required to accumulate to maximal levels to stimulate entry into mitosis. Importantly, when G2/M cyclins reach maximal levels, the ubiquitin-proteosome system is activated to destroy the G2/M cyclin (Bastians et al., 1999). Upon the subsequent destruction or degradation of the cyclin, the cell progresses past metaphase toward completion of mitosis. In one embodiment of the invention, the anti-cell proliferation polypeptide comprises a portion of a G2/M cyclin, preferably a vertebrate cyclin B, more preferably a mammalian cyclin B, or most preferably a human cyclin B. SEQ ID NO:1 depicts the human cyclin B2 full length cDNA sequence. SEQ ID NO:2 depicts the human cyclin B2 polypeptide sequence. Polynucleotide and/or protein sequences to many eukaryotic G2/M cyclins are freely available in the GenBank database. Table 1 provides exemplary information to assist the artisan in the procurement of sequences useful in the practice of this embodiment of the invention. However, it is understood that the scope of the invention encompasses G2/M cyclins which are not be listed in Table 1, but which nonetheless are known in the art or discovered in the future as G2/M cyclins.

TABLE 1

Examples of G2/M Cyclins1

| Organism and molecule | Genbank Accession Number |
| --- | --- |
| goldfish cyclin B | S48758 |
| mouse cyclin B1 | X64713 |
| C. elegans cyclin B | U20903 |
| Oryza sativa G2/M cyclin | X82036 |
| Dictyostelium clb | U110506 |
| Saccharomyces cyclin B | M62389 |
| Xenopus laevis cyclin B2 | J03167 |

In another embodiment, the cell cycle effector domain of the chimeric peptide comprises residues 1–70 of cyclin B, or the equivalent in other G2/M cyclins, preferably a vertebrate cyclin B, more preferably a mammalian cyclin B, or most preferably a human cyclin B. This portion of a cyclin is comprised of the D-box which is required for the destruction of cyclins by the ubiquitin/proteosome pathway. It is known in the art that lysine residues in the D-box region associate with ubiquitin (King et al., 1996, Mol. Biol. Cell 7:1343–1357). Peptides consisting of a functional D-box competitively inhibit the degradation of some cyclin B homologues (Yamano et al., 1998, EMBO J. 17:5670–5678. The D-box containing region of human cyclin B2 D-box region is shown in SEQ ID NO:3.

In an alternate embodiment, the cell cycle effector comprises a portion of a mutant G2/M cyclin, wherein the D-box contains one or several mutations which inhibit the ubiquitin-mediated proteolysis of said cyclin. The D-box of human cyclin B2 comprises amino acids 32–40 of SEQ ID NO:3. The cyclin comprising a D-box mutation is preferably a vertebrate cyclin B, more preferably a mammalian cyclin B, or most preferably a human cyclin B. SEQ ID NO:4 shows an exemplary human cyclin B2 comprising a D-box mutation. The skilled artisan, upon reviewing the paper by King et al.(1996), would readily know that many different amino acid substitutions, insertions or deletions within the D-box, which are included within the scope of this invention, can interfere with ubiquitin-mediated proteolysis.

In yet another embodiment, the cell cycle effector domain of the chimeric polypeptide comprises a portion of a c-Mos polypeptide, preferably a vertebrate c-Mos polypeptide, more preferably a mammalian c-Mos polypeptide, or most preferably a human c-Mos polypeptide. c-Mos is a protein kinase which functions as a cytostatic factor (CSF) in oocytes. During oocyte maturation, mature secondary oocytes are arrested in metaphase of meiosis II, awaiting activation by the sperm. This metaphase arrest is attributed to the activity of CSF (Gilbert, 1997.) The polynucleotide sequence and polypeptide sequence of human c-Mos are presented as SEQ ID NOS:5 and 6, respectively. Examples of additional vertebrate c-Mos homologues are presented in Table 2.

TABLE 2

Examples of Vertebrate c-Mos

| Organism and molecule | Genbank Accession Number |
| --- | --- |
| Xenopus laevis c-Mos | X13311 |
| rat c-Mos | X52952 |
| mouse c-Mos | NM_020021 |

The transit peptide domain of the chimeric peptide comprises an hydrophobic or cationic/amphipathic sequence which enables the chimeric peptide to cross the plasma membranes of cells. Hydrophobic sequences may comprise portions of the membrane permeable sequences of Karposi FGF, Grb2 or integrin β3, the fusion sequence of HIV-1 gb41 or the signal sequence of Caiiman croc. Ig(v) light chain. Amphipathic/cationic sequences may comprise portions of influenza hemagglutinin subunit, antennapedia third helix, HIV-1 Tat, HSV transcription factor, galanin/mastoparin fusion or synthetic analogs thereof. For a review of transit peptides, see Gariepy and Kawamura, 2001. Examples of useful peptides which fall within the scope of the invention are described in Table 3. The preferred transit peptide comprises an HIV-1 Tat sequence of SEQ ID NO:18 (Gly Arg Lys Lys Arg Arg Gln Arg).

In the preferred embodiment of the invention, the chimeric peptide comprises a N-terminal HIV-1 Tat domain fused in frame with the coding sequence of wild-type human cyclin B2 (human Tat-cyclin B). SEQ ID NO:21 and 22 describe the nucleotide and protein sequence, respectively, of human Tat-cyclin B.

The present invention is also directed to polynucleotides encoding any of the above described polypeptides. The polynucleotide may be produced by any method known in the art. Preferably, it is produced by the polymerase chain reaction (PCR) using a 5' primer comprising a transit peptide coding sequence followed in frame by at least 5 nucleotides, preferably 20 nucleotides encoding the N-terminal portion of the cell cycle effector domain and a 3' primer comprising the C-terminal coding region of the cell cycle effector domain. The template for the PCR is a DNA which encodes a cell cycle effector. The PCR product is ligated into the multiple cloning site of an expression vector, which vector may be a plasmid, viral phage, artificial chromosome or cosmid that is capable of independent replication and protein production in bacteria, yeast, insect, or mammalian cells. Methods of PCR, ligation and cell transformation are well known in the art and are described in sufficient detail at least in Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

TABLE 3

Transit Peptides (see Gariepy and Kawamura, 2001).

| Source | Sequence | |
|---|---|---|
| Kaposi FGF | AAVALLPAVLLALLAP | SEQ ID NO:7 |
| Grb2 (SH2 domain) | AAVLLPVLLAAP | SEQ ID NO:8 |
| Integrin □3 | VTVLALGALAGVGVG | SEQ ID NO:9 |
| HIV-1 gp41 (1–23) | GALFLGFLGAAGSTMGA | SEQ ID NO:10 |
| Ig(v) light chain | MGLGLHLLVLAAALQGAMGLGLHLLLAAALQGA | SEQ ID NO:11 |
| Influenza HA-2 | WEAKLAKALAKALAKHLAKALAKALKACEA | SEQ ID NO:12 |
| Influenza HA-2 | WEAALAEALAEALAEHLAEALAEALEALAA | SEQ ID NO:13 |
| 4$_6$ | LARLLARLLARLLRALLRALLRAL | SEQ ID NO:14 |
| Hel 11-7 | KLLKLLLKLWKLLLKLLK | SEQ ID NO:15 |
| Antennapedia (43–58) | RQIKIWFQRRMKKWK | SEQ ID NO:16 |
| HIV-Tat (47–57) | YGRKKRRQRRR | SEQ ID NO:17 |
| HIV-Tat (48–55) | GRKKRRQR | SEQ ID NO:18 |
| HSC transcription factor | DAATATRGRSAASRPTERPRAPARSASRPRRPVE | SEQ ID NO:19 |
| Galanin + Mastoparan | GWTLNSAGYLLGKINLKALAALAKKIL | SEQ ID NO:20 |

In another embodiment, the invention is directed to an isolated or purified polynucleotide encoding either a G2/M cyclin, a D-box domain, a mutant G2/M cyclin comprising a D-box inactivating mutation, or a c-Mos, as described above and in SEQ ID NOS:1–6, operably linked to a promoter that produces expression of the cell cycle modulator in the cell. The polynucleotide can comprise an expression plasmid, a virus vector, or other vector used in the art to deliver genes into cells.

In another embodiment of the invention, the polynucleotide may be used to treat cells or tissues within a living patient, wherein the patient suffers from a benign or malignant hyperplasia. The polynucleotide is preferably selectively delivered to target cells within the patient so as not to affect non-target tissues. Targeted delivery of the polynucleotide can be effected, for example, by using delivery vehicles such as polycations, liposomes, or viral vectors containing targeting moieties that recognize and bind a specific marker on the target cell. For example, in the treatment of skin hyperplasias, the treating composition comprising the polynucleotide may be topically applied to the skin. Such methods are known in the art, see, e.g., U.S. Pat. Nos. 5,635,383 and 5,314,688 and Foldvari et al., 1999. Another targeted delivery approach uses viral vectors that can only replicate in specific cell types which is accomplished by placing the viral genes necessary for replication under the transcriptional control of a response element for a transcription factor that is only active in the target cell. See, e.g., U.S. Pat. No. 5,698,443.

Another embodiment of the invention is directed to treating patients by administering pharmaceutical compositions comprising a chimeric polypeptide which inhibits cell proliferation consisting of at least a transit peptide domain and a cell cycle effector, e.g., Tat-cyclin B, wherein the patient suffers from a benign or malignant hyperplasia. Compositions comprising the chimeric polypeptide can be administered to a patient by any suitable route known in the art including, for example, intravenous, subcutaneous, intramuscular, transdermal, intrathecal, intraurethral, rectal or intracerebral. Administration can be either rapid as by injection or over a period of time as by slow infusion or administration of a slow release formulation. For treating cells in the central nervous system, administration can be by injection into the cerebrospinal fluid.

It is contemplated that the compositions of the present invention are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is contemplated that certain formulations comprising the chimeric polypeptide, which inhibits cell proliferation, that are specifically directed to skin hyperplasias, such as psoriasis, are to be administered topically as a gel, cream or lotion. Such formulations may include penetration enhancers such as N-alkylazacycloheptanones, n-decylmethyl sulfoxide, surfactants and/or a urea/ethanol/menthol/camphor/methyl salicylate hydroxypropylcellulose gel. Pharmaceutical formulations may also include encapsulating microspheres, nanoparticles or liposomes. Liposomes may be composed of dipalmitoyl phosphatidylcholine /cholesterol, non-ionic detergents such as glyceryl dilaurate cholesterol /polyoxyethylene-10-stearyl ether or mixtures of phosphatidylcholine /sodium cholate.

It is also contemplated that certain formulations comprising the chimeric polypeptide agent are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic and nucleic acid degradation and/or substances which promote absorption such as, for example, surface active agents.

The chimeric polypeptide or recombinant polynucleotide agent is administered to patients, wherein the patient may be a human or an animal, in an amount effective to decrease or inhibit cell proliferation of target cells within the patient. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in HeLa cell proliferation assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

The compositions and methods of the present invention provide remedies for disorders which are characterized as hyperplasias or neoplasias, including various forms of psoriasis, eczema, seborrhea, benign prostate hyperplasia, adrenal hyperplasia, endometrial hyperplasia, squamous cell hyperplasia, sebaceous hyperplasia, and various cancers. The remedies are achieved through the treatment of tissues and cells that are affected by the disorders with agents that block cell cycle progression. These remedies represent improvements in treatments for these disorders.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press, which are both incorporated by reference.

All references cited here in the specification are incorporated by reference.

EXAMPLE 1

Production of Recombinant Tat-cyclin B (a) Construction of the Tat-cyclin B Polynucleotide by Polymerase Chain Reaction Oligonucleotide primers 5'TatclnB (SEQ ID NO:23) and 3'TatclnB (SEQ ID NO:24) are mixed together with a template DNA comprising cyclin B, then subjected to the polymerase chain reaction. The cyclin B template DNA was isolated from the bacterial IMAGE consortium clone no. 1499287. Oligonucleotide primer 5'TatclnB (SEQ ID NO. 23) is comprised of 25 HIV-1 Tat nucleotides (position 10–34), 21 cyclin B nucleotides from the 5' end of the cyclin B gene (position 35–55), and an EcoRI restriction endonuclease site (position 5–9). The 3'TatclnB oligonucleotide primer is comprised of 22 nucleotides from the 3' end of the cyclin B gene (position 13–34), and a NotI restriction endonuclease site (position 5–12). The PCR reaction mixture consisted of template DNA at 0.1 volume, each oligonucleotide primer at 0.5 μM, 25 mM TAPS (pH9.3), 50 mM KCl, 1 mM 2-mercaptoethanol, 2 mM $MgCl_2$, 0.4 mM each deoxynucleotide triphosphate, 0.25 U/μL of ExTaq™ (Takara, LTD, Otsu, Shiga, Japan) thermostable DNA polymerase. The PCR reaction parameters were as follows: 94° C. for 5 minutes, for 1 cycle; 94° C. for 1 minute, 50° C. for 2 minutes, 72° C. for 3 minutes, for 25 to 30 cycles; 72° C. for 10 minutes, for 1 cycle. FIG. 1 is 1% agarose gel stained with ethidium bromide depicting the ~1320 bp Tat-cyclin B PCR product in lane 2. Lane 1 contains DNA markers of the size indicated on the Y axis of the gel.

(b) Construction of the pGAP-ZαA—Tat-cyclin B Plasmid

The Tat-cyclin B PCR product is purified by phenol/chloroform extraction and ethanol precipitation, then digested with the restriction enzymes EcoRI and NotI. The digested Tat-cyclin B construct is again is purified by phenol/chloroform extraction and ethanol precipitation, followed by ligation into a pGAP-ZαA vector (Invitrogen Corp, Carlsbad, Calif.) that was predigested with EcoRI and NotI. The insert to vector ratio was 3 to 1 and the ligation reaction was carried out in an excess of ligase for at least 3 hours at room temperature. Competent XL1-BLUE™ cells (Stratagene, LaJolla, Calif.), which are a strain of E. coli well known in the art, prepared by the $CaCl_2$ method (Sambrook et al.) were transformed with the pGAP-ZαA—Tat-cyclin B ligation mixture, and plated onto low salt LB agar containing the antibiotic Zeocin. For further details on methodology, see "Pichia expression vectors for constitutive expression and purification of recombinant proteins", version C, 2000, which is herein incorporated by reference.

Figure 2:
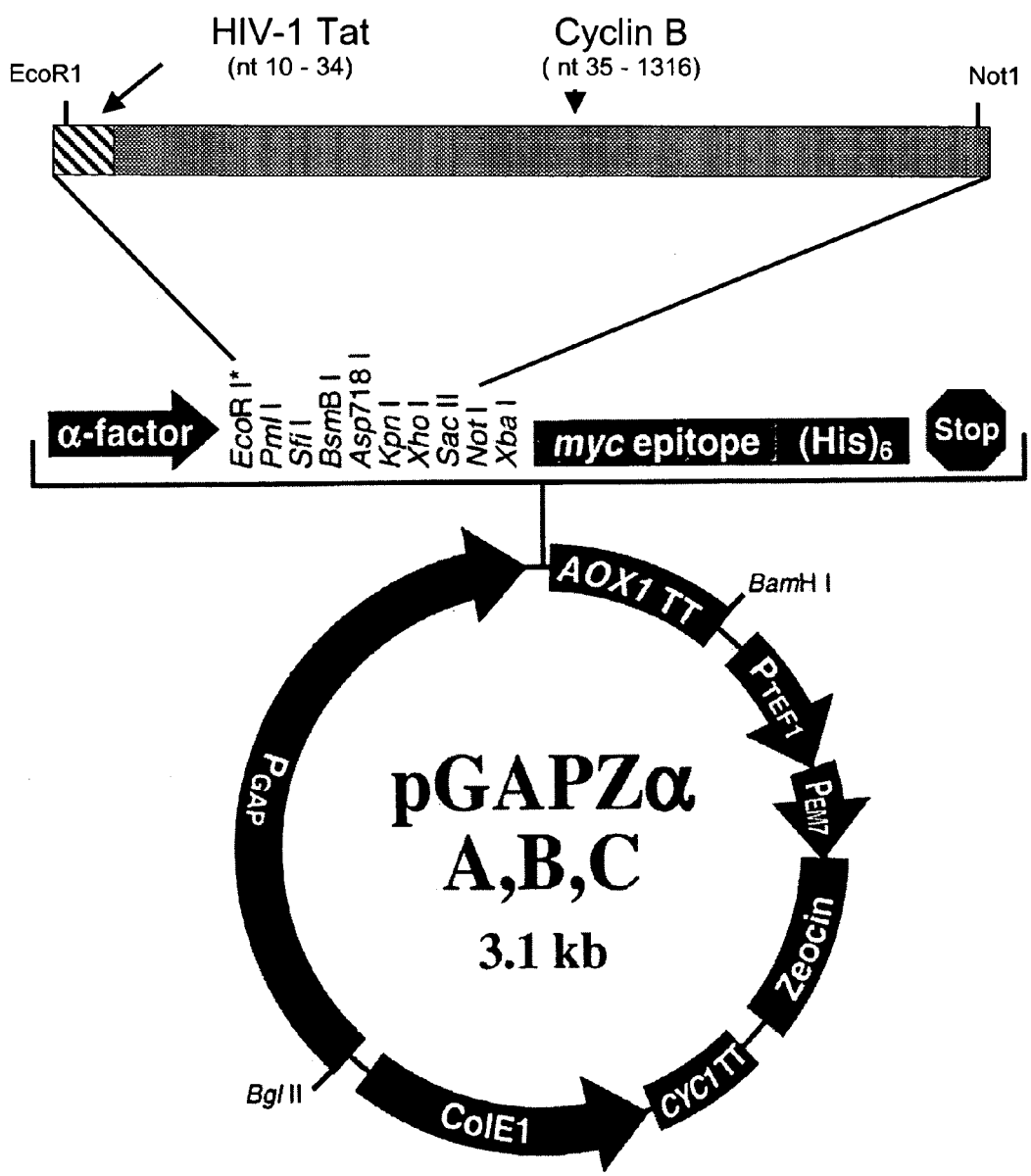
FIG. 2 depicts the plasmid vector pGAP-Z-alphaA-Tat-clnB, which encodes for the secreted form of Tat-clnB chimeric peptide.

Bacterial colonies harboring the pGAP-ZαA—Tat-cyclin B plasmid were identified via colony PCR using the 5'TatclnB and 3' TatclnB primer set. pGAP-ZαA—Tat-cyclin B plasmid DNA was prepared by the boiling method from expanded cultures of bacteria. A diagram of the pGAP-ZαA—Tat-cyclin B plasmid is shown in FIG. 2.

EXAMPLE 2

Expression and Isolation of Tat-cyclin B Peptide pGAP-ZαA—Tat-cyclin B plasmid DNA was transformed into a strain of *Pichia angusta* (formerly *Hansenula polymorpha*). Transformation competent *Pichia angusta* cells were prepared according to the $LiCl_2$ modification of the well known Lithium acetate yeast transformation method. See the handbook entitled "Pichia expression vectors for constitutive expression and purification of recombinant proteins", version C, 2000, for additional details on the transformation methodology. *Pichia angusta* transformed with pGAP-ZαA—Tat-cyclin B plasmid DNA were plated onto yeast extract-peptone-dextrose (YPD)-agar containing Zeocin and colonies harboring the correct plasmid were selected via colony PCR, as described in example 1.

Transformed *Pichia* were grown in liquid YPD media to a cell density corresponding to an optical density at 600 nm of about 1.0 (±0.5). The cells were pelleted by centrifugation and the supernatant was filter sterilized through a 0.22 micron filter. The supernatant, which contains Tat-cyclin B, was concentrated ten-fold using CENTRICON PLUS YM-10® concentrators (Millipore, Bedford, Mass.). Alternatively, the recombinant Tat-cyclin B may be further concentrated and/or purified using methods well known in the art, such as, for example affinity chromatography.

Isolated and purified Tat-cyclin B polypeptide may be quantitated by quantitative Western blot analysis, the Biuret method, the BCA method, the Bradford coomassie-blue binding method or any methods for protein determination that are known in the art.

EXAMPLE 3

Treatment of HELA Cells with Tat-cyclin B Peptide and Demonstration of Cell Cycle Arrest HeLa cells (ATCC No. CCL-2)were maintained in standard HeLa cell media consisting of minimum essential medium Eagle with 2 mM L-glutamine and Earle's BSS adjusted to contain 1.5 g/L sodium bicarbonate, 0.1 mM non-essential amino acids, and 1.0 mM sodium pyruvate, 90%; fetal bovine serum, 10%; at 37° C. in an atmosphere of 5% CO2.

Adherent HeLa cells were harvested from the tissue culture plates by standard trypsin/EDTA treatment, washed in sterile PBS and resuspended in fresh growth media. $5 \times 10^4$ cells were plated onto each of 6, 100-mm tissue culture plates. Two cultures were incubated with 10 ml standard HeLa cell media plus 100 µl sterile YPD, two different cultures with 10 ml media plus 100 µl conditioned YPD media containing Tat-cyclin B and the final two cultures with 100 µl concentrated YPD media containing 10-fold concentrated Tat-cyclin B. Cells were grown for approximately four days at 37° C./5% $CO_2$, then harvested and counted in a hemocytometer. Table 4 presents the approximate number of cells determined to be in each culture after four days.

TABLE 4

HeLa cell counts

| treatment | No. of cells | approximate no. of cell doublings |
|---|---|---|
| YPD | $1.4 \times 10^6$ | ~6 |
| YPD | $1.2 \times 10^6$ | ~5 |
| undiluted-conditioned YPD | $1.4 \times 10^6$ | ~6 |
| undiluted-conditioned YPD | $1.04 \times 10^6$ | ~4.5 |
| 10X concentrated-conditioned YPD | $8.8 \times 10^4$ | ~0.8 |
| 10X concentrated-conditioned YPD | $1.05 \times 10^5$ | ~1.1 |

The results presented in Table 4 clearly demonstrate the effectiveness of Tat-cyclin B to arrest rapidly proliferating cells. Furthermore, it is important to note that the cells in each culture, including the experimental cultures, looked healthy and showed none of the obvious signs of necrosis or apoptosis.

EXAMPLE 4

Mouse Tail Test Model

The mouse tail test is a well known assay employed to assess the effectiveness of topical anti-psoriatic treatments (Sebok et al., 2000). Tat-cyclin B at a concentration of 0.01%, 0.1%, 1.0%, and 10% (v/v) in a gel, cream or ointment is applied to adult mouse tails. Control mice are treated with vehicle alone. After two weeks of treatment, longitudinal histological sections are prepared from the tail skin and examined for orthokeratosis by methods well known in the art.

What is claimed:

1. An isolated polynucleotide comprising a nucleic acid encoding the polypeptide sequence set forth in SEQ ID NO:22.

2. The polynucleotide of claim 1 wherein the polynucleotide is-operably linked to a promoter.

3. The polynucleotide of claim 2, wherein the polynucleotide is part of a vector for expression of recombinant proteins in a host cell.

4. The polynucleotide of claim 3 wherein the host cell is selected from the group consisting of a cell in a cell in a transgenic plant, a yeast cell, an insect cell and a mammalian cell.

5. The polynucleotide of claim 4 wherein the host cell is a *Pichia pastoris* cell.

6. A *Pichia pastoris* cell comprising a polynucleotide sequence that encodes a polypeptide sequence comprising SEQ ID NO:22.

* * * * *

SEQUENCE LISTING

```
<160> NUMBER OF SEQ ID NOS: 25

<210> SEQ ID NO 1
<211> LENGTH: 1530
<212> TYPE: DNA
<213> ORGANISM: Homo sapiens
<300> PUBLICATION INFORMATION:
<301> AUTHORS: Liu, J.H.
              Wei, S.
              Burnette, P.K.
              Gamero, A.M.
              Hutton, M
              Djeu, J.Y.
<302> TITLE: Functional association of TGF-beta receptor II with
              cyclin B
<303> JOURNAL: Oncogene
```

<304> VOLUME: 18
<305> ISSUE: 1
<306> PAGES: 269-275
<307> DATE: 1999-01-07
<308> DATABASE ACCESSION NUMBER: Genbank Accession No. NM_004701
<309> DATABASE ENTRY DATE: 2000-11-01

<400> SEQUENCE: 1

```
aatcctggaa caaggctaca gcgtcgaaga tccccagcgc tgcgggctcg gagagcagtc    60
ctaacggcgc ctcgtacgct agtgtcctcc cttttcagtc cgcgtccctc cctgggccgg   120
gctggcactc ttgccttccc cgtccctcat ggcgctgctc cgacgcccga cggtgtccag   180
tgatttggag aatattgaca caggagttaa ttctaaagtt aagagtcatg tgactattag   240
gcgaactgtt ttagaagaaa ttggaaatag agttacaacc agagcagcac aagtagctaa   300
gaaagctcag aacaccaaag ttccagttca acccaccaaa acaacaaatg tcaacaaaca   360
actgaaacct actgcttctg tcaaaccagt acagatggaa aagttggctc aaagggtcc   420
ttctcccaca cctgaggatg tctccatgaa ggaagagaat ctctgccaag cttttctga   480
tgccttgctc tgcaaaatcg aggacattga taacgaagat tgggagaacc ctcagctctg   540
cagtgactac gttaaggata tctatcagta tctcaggcag ctggaggttt tgcagtccat   600
aaacccacat ttcttagatg aagagatat aaatggacgc atgcgtgcca tcctagtgga   660
ttggctggta caagtccact ccaagtttag gcttctgcag gagactctgt acatgtgcgt   720
tggcattatg gatcgatttt tacaggttca gccagtttcc cggaagaagc ttcaattagt   780
tgggattact gctctgctct tggcttccaa gtatgaggag atgttttctc caaatattga   840
agactttgtt tacatcacag acaatgctta taccagttcc caaatccgag aaatggaaac   900
tctaattttg aaagaattga aatttgagtt gggtcgaccc ttgccactac acttcttaag   960
gcgagcatca aaagccgggg aggttgatgt tgaacagcac actttagcca agtatttgat  1020
ggagctgact ctcatcgact atgatatggt gcattatcat ccttctaagg tagcagcagc  1080
tgcttcctgc ttgtctcaga aggttctagg acaaggaaaa tggaacttaa agcagcagta  1140
ttacacagga tacacagaga atgaagtatt ggaagtcatg cagcacatgg ccaagaatgt  1200
ggtgaaagta aatgaaaact taactaaatt catcgccatc aagaataagt atgcaagcag  1260
caaactcctg aagatcagca tgatccctca gctgaactca aaagccgtca agaccttgc  1320
ctccccactg ataggaaggt cctaggctgc cgtgggccct ggggatgtgt gcttcattgt  1380
gcccttttc ttattggttt agaactcttg attttgtaca tagtcctctg gtctatctca  1440
tgaaacctct tctcagacca gttttctaaa catatattga ggaaaaataa agcgattggt  1500
ttttcttaag gtaaaaaaaa aaaaaaaaa                                    1530
```

<210> SEQ ID NO 2
<211> LENGTH: 398
<212> TYPE: PRT
<213> ORGANISM: Homo sapiens
<300> PUBLICATION INFORMATION:
<301> AUTHORS: Liu, J.H.
           Wei, S.
           Burnette, P.K.
           Gamero, A.M.
           Hutton, M
           Djeu, J.Y.
<302> TITLE: Functional association of TGF-beta receptor II with cyclin B
<303> JOURNAL: Oncogene
<304> VOLUME: 18
<305> ISSUE: 1
<306> PAGES: 269-275

-continued

<307> DATE: 1999-01-07
<308> DATABASE ACCESSION NUMBER: Genbank Accession No. NM_004701
<309> DATABASE ENTRY DATE: 2000-11-01

<400> SEQUENCE: 2

```
Met Ala Leu Leu Arg Arg Pro Thr Val Ser Ser Asp Leu Glu Asn Ile
                5                   10                  15

Asp Thr Gly Val Asn Ser Lys Val Lys Ser His Val Thr Ile Arg Arg
            20                  25                  30

Thr Val Leu Glu Glu Ile Gly Asn Arg Val Thr Thr Arg Ala Ala Gln
        35                  40                  45

Val Ala Lys Lys Ala Gln Asn Thr Lys Val Pro Val Gln Pro Thr Lys
    50                  55                  60

Thr Thr Asn Val Asn Lys Gln Leu Lys Pro Thr Ala Ser Val Lys Pro
65                  70                  75                  80

Val Gln Met Glu Lys Leu Ala Pro Lys Gly Pro Ser Pro Thr Pro Glu
                85                  90                  95

Asp Val Ser Met Lys Glu Glu Asn Leu Cys Gln Ala Phe Ser Asp Ala
            100                 105                 110

Leu Leu Cys Lys Ile Glu Asp Ile Asp Asn Glu Asp Trp Glu Asn Pro
        115                 120                 125

Gln Leu Cys Ser Asp Tyr Val Lys Asp Ile Tyr Gln Tyr Leu Arg Gln
    130                 135                 140

Leu Glu Val Leu Gln Ser Ile Asn Pro His Phe Leu Asp Gly Arg Asp
145                 150                 155                 160

Ile Asn Gly Arg Met Arg Ala Ile Leu Val Asp Trp Leu Val Gln Val
                165                 170                 175

His Ser Lys Phe Arg Leu Leu Gln Glu Thr Leu Tyr Met Cys Val Gly
            180                 185                 190

Ile Met Asp Arg Phe Leu Gln Val Gln Pro Val Ser Arg Lys Lys Leu
        195                 200                 205

Gln Leu Val Gly Ile Thr Ala Leu Leu Leu Ala Ser Lys Tyr Glu Glu
    210                 215                 220

Met Phe Ser Pro Asn Ile Glu Asp Phe Val Tyr Ile Thr Asp Asn Ala
225                 230                 235                 240

Tyr Thr Ser Ser Gln Ile Arg Glu Met Glu Thr Leu Ile Leu Lys Glu
                245                 250                 255

Leu Lys Phe Glu Leu Gly Arg Pro Leu Pro Leu His Phe Leu Arg Arg
            260                 265                 270

Ala Ser Lys Ala Gly Glu Val Asp Val Glu Gln His Thr Leu Ala Lys
        275                 280                 285

Tyr Leu Met Glu Leu Thr Leu Ile Asp Tyr Asp Met Val His Tyr His
    290                 295                 300

Pro Ser Lys Val Ala Ala Ala Ser Cys Leu Ser Gln Lys Val Leu
305                 310                 315                 320

Gly Gln Gly Lys Trp Asn Leu Lys Gln Gln Tyr Tyr Thr Gly Tyr Thr
                325                 330                 335

Glu Asn Glu Val Leu Glu Val Met Gln His Met Ala Lys Asn Val Val
            340                 345                 350

Lys Val Asn Glu Asn Leu Thr Lys Phe Ile Ala Ile Lys Asn Lys Tyr
        355                 360                 365

Ala Ser Ser Lys Leu Leu Lys Ile Ser Met Ile Pro Gln Leu Asn Ser
    370                 375                 380

Lys Ala Val Lys Asp Leu Ala Ser Pro Leu Ile Gly Arg Ser
```

```
                385                 390                 395

<210> SEQ ID NO 3
<211> LENGTH: 70
<212> TYPE: PRT
<213> ORGANISM: Homo sapiens

<400> SEQUENCE: 3

Met Ala Leu Leu Arg Arg Pro Thr Val Ser Ser Asp Leu Glu Asn Ile
                 5                  10                  15

Asp Thr Gly Val Asn Ser Lys Val Lys Ser His Val Thr Ile Arg Arg
             20                  25                  30

Thr Val Leu Glu Glu Ile Gly Asn Arg Val Thr Thr Arg Ala Ala Gln
         35                  40                  45

Val Ala Lys Lys Ala Gln Asn Thr Lys Val Pro Val Gln Pro Thr Lys
     50                  55                  60

Thr Thr Asn Val Asn Lys
 65                  70

<210> SEQ ID NO 4
<211> LENGTH: 398
<212> TYPE: PRT
<213> ORGANISM: Homo sapiens
<220> FEATURE:
<221> NAME/KEY: Site
<222> LOCATION: (32)
<223> OTHER INFORMATION: arginine or alanine
<220> FEATURE:
<221> NAME/KEY: Site
<222> LOCATION: (35)
<223> OTHER INFORMATION: leucine or alanine
<220> FEATURE:
<221> NAME/KEY: Site
<222> LOCATION: (38)
<223> OTHER INFORMATION: isoleucine or alanine
<220> FEATURE:
<221> NAME/KEY: Site
<222> LOCATION: (40)
<223> OTHER INFORMATION: asparagine or alanine

<400> SEQUENCE: 4

Met Ala Leu Leu Arg Arg Pro Thr Val Ser Ser Asp Leu Glu Asn Ile
                 5                  10                  15

Asp Thr Gly Val Asn Ser Lys Val Lys Ser His Val Thr Ile Arg Xaa
             20                  25                  30

Thr Val Xaa Glu Glu Xaa Gly Xaa Arg Val Thr Thr Arg Ala Ala Gln
         35                  40                  45

Val Ala Lys Lys Ala Gln Asn Thr Lys Val Pro Val Gln Pro Thr Lys
     50                  55                  60

Thr Thr Asn Val Asn Lys Gln Leu Lys Pro Thr Ala Ser Val Lys Pro
 65                  70                  75                  80

Val Gln Met Glu Lys Leu Ala Pro Lys Gly Pro Ser Pro Thr Pro Glu
                 85                  90                  95

Asp Val Ser Met Lys Glu Glu Asn Leu Cys Gln Ala Phe Ser Asp Ala
            100                 105                 110

Leu Leu Cys Lys Ile Glu Asp Ile Asp Asn Glu Asp Trp Glu Asn Pro
        115                 120                 125

Gln Leu Cys Ser Asp Tyr Val Lys Asp Ile Tyr Gln Tyr Leu Arg Gln
    130                 135                 140

Leu Glu Val Leu Gln Ser Ile Asn Pro His Phe Leu Asp Gly Arg Asp
145                 150                 155                 160
```

-continued

```
Ile Asn Gly Arg Met Arg Ala Ile Leu Val Asp Trp Leu Val Gln Val
            165                 170                 175
His Ser Lys Phe Arg Leu Leu Gln Glu Thr Leu Tyr Met Cys Val Gly
            180                 185                 190
Ile Met Asp Arg Phe Leu Gln Val Gln Pro Val Ser Arg Lys Lys Leu
        195                 200                 205
Gln Leu Val Gly Ile Thr Ala Leu Leu Leu Ala Ser Lys Tyr Glu Glu
    210                 215                 220
Met Phe Ser Pro Asn Ile Glu Asp Phe Val Tyr Ile Thr Asp Asn Ala
225                 230                 235                 240
Tyr Thr Ser Ser Gln Ile Arg Glu Met Glu Thr Leu Ile Leu Lys Glu
                245                 250                 255
Leu Lys Phe Glu Leu Gly Arg Pro Leu Pro Leu His Phe Leu Arg Arg
            260                 265                 270
Ala Ser Lys Ala Gly Glu Val Asp Val Glu Gln His Thr Leu Ala lys
        275                 280                 285
Tyr Leu Met Glu Leu thr Leu Ile Asp Tyr Asp Met Val His Tyr His
    290                 295                 300
Pro Ser Lys Val Ala Ala Ala Ser Cys Leu Ser Gln Lys Val Leu
305                 310                 315                 320
Gly Gln Gly Lys Trp Asn Leu Lys Gln Gln Tyr Tyr Thr Gly Tyr Thr
                325                 330                 335
Glu Asn Glu val Leu Glu Val Met Gln His Met Ala Lys Asn Val Val
            340                 345                 350
Lys Val Asn Glu Asn Leu Thr Lys Phe Ile Ala Ile Lys Asn Lys Tyr
        355                 360                 365
Ala Ser Ser Lys Leu Leu Lys Ile Ser Met Ile Pro Gln Leu Asn Ser
    370                 375                 380
Lys Ala Val Lys Asp Leu Ala Ser Pro Leu Ile Gly Arg Ser
385                 390                 395
```

<210> SEQ ID NO 5
<211> LENGTH: 1041
<212> TYPE: DNA
<213> ORGANISM: Homo sapiens
<300> PUBLICATION INFORMATION:
<301> AUTHORS: Watson, R.
              Oskaesson, M.
              Vande Woude, G.F.
<302> TITLE: Human DNA sequence homologous to the transforming gene
             (mos) of Moloney murine sarcoma virus.
<303> JOURNAL: EMBO J.
<304> VOLUME: 4
<305> ISSUE: 9
<306> PAGES: 2245-2248
<307> DATE: 1982-01-07
<308> DATABASE ACCESSION NUMBER: Genbank Accession No. NM_004701
<309> DATABASE ENTRY DATE: 2000-11-01

<400> SEQUENCE: 5

```
atgccctcgc ccctggccct acgccctac  ctccggagcg agttttcccc atcggtggac     60
gcgcggccct gcagcagtcc ctcagagcta cctgcgaagc tgcttctggg ggccactctt    120
cctcgggccc cgcggctgcc gcgccggctg gcctggtgct ccattgactg ggagcaggtg    180
tgcttgctgc agaggctggg agctggaggg tttggctcgg tgtacaaggc gacttaccgc    240
ggtgttcctg tggccataaa gcaagtgaac aagtgcacca agaaccgact agcatctcgg    300 cggagttct ggctgagct caacgtagca aggctgcgcc acgataacat cgtgcgcgtg    360
gtggctgcca gcacgcgcac gcccgcaggg tccaatagcc tagggaccat catcatggag    420
```

-continued

```
ttcggtggca acgtcacttt acaccaagtc atctatggcg ccgccggcca ccctgagggg    480
gacgcagggg agcctcactg ccgcactgga ggacagttaa gtttgggaaa gtgtctcaag    540
tactcactag atgttgtgaa cggcctgctc ttcctccact cgcaaagcat tgtgcacttg    600
gacctgaagc ccgcgaacat cttgatcagt gagcaggatg tctgtaaaat tagtgacttc    660
ggttgctctg agaagttgga agatctgctg tgcttccaga caccctctta ccctctagga    720
ggcacataca cccaccgcgc cccggagctc ctgaaaggag agggcgtgac gcctaaagcc    780
gacatttatt cctttgccat cactctctgg caaatgacta ccaagcaggc gccgtattcg    840
ggggagcggc agcacatact gtacgcggtg gtggcctacg acctgcgccc gtccctctcc    900
gctgccgtct tcgaggactc gctccccggg cagcgccttg gggacgtcat ccagcgctgc    960
tggagaccca gcgcggcgca gaggccgagc gcgcggctgc ttttggtgga tctcacctct   1020
ttgaaagctg aactcggctg a                                             1041
```

<210> SEQ ID NO 6
<211> LENGTH: 346
<212> TYPE: PRT
<213> ORGANISM: Homo sapiens
<300> PUBLICATION INFORMATION:
<301> AUTHORS: Watson, R.
              Oskaesson, M.
              Vande Woude, G.F.
<302> TITLE: Human DNA sequence homologous to the transforming gene
              (mos) of Moloney murine sarcoma virus.
<303> JOURNAL: EMBO J.
<304> VOLUME: 4
<305> ISSUE: 9
<306> PAGES: 2245-2248
<307> DATE: 1982-01-07
<308> DATABASE ACCESSION NUMBER: Genbank Accession No. NM_004701
<309> DATABASE ENTRY DATE: 2000-11-01

<400> SEQUENCE: 6

Met Pro Ser Pro Leu Ala Leu Arg Pro Tyr Leu Arg Ser Glu Phe Ser
                 5                  10                  15

Pro Ser Val Asp Ala Arg Pro Cys Ser Ser Pro Ser Glu Leu Pro Ala
             20                  25                  30

Lys Leu Leu Leu Gly Ala Thr Leu Pro Arg Ala Pro Arg Leu Pro Arg
         35                  40                  45

Arg Leu Ala Trp Cys Ser Ile Asp Trp Glu Gln Val Cys leu Leu Gln
     50                  55                  60

Arg Leu Gly Ala Gly Gly Phe Gly Ser Val Tyr Lys Ala Thr Tyr Arg
65                  70                  75                  80

Gly Val Pro Val Ala Ile Lys Gln Val Asn Lys Cys Thr Lys Asn Arg
                 85                  90                  95

Leu Ala Ser Arg Arg Ser Phe Trp Ala Glu Leu Asn Val Ala Arg Leu
            100                 105                 110

Arg His Asp Asn Ile Val Arg Val Val Ala Ala Ser Thr Arg Thr Pro
        115                 120                 125

Ala Gly Ser Asn Ser Leu Gly Thr Ile Ile Met Glu Phe Gly Gly Asn
    130                 135                 140

Val Thr Leu His Gln Val Ile Tyr Gly Ala Ala Gly His Pro Glu Gly
145                 150                 155                 160

Asp Ala Gly Glu Pro His Cys Arg Thr Gly Gly Gln Leu Ser Leu Gly
                165                 170                 175

Lys Cys Leu Lys Tyr Ser Leu Asp Val Val Asn Gly Leu Leu Phe Leu
            180                 185                 190

```
His Ser Gln Ser Ile Val His Leu Asp Leu Lys Pro Ala Asn Ile Leu
        195                 200                 205

Ile Ser Glu Gln Asp Val Cys Lys Ile Ser Asp Phe Gly Cys Ser Glu
210                 215                 220

Lys Leu Glu Asp Leu Leu Cys Phe Gln Thr Pro Ser Tyr Pro Leu Gly
225                 230                 235                 240

Gly Thr Tyr Thr His Arg Ala Pro Glu Leu Leu Lys Gly Glu Gly Val
                245                 250                 255

Thr Pro Lys Ala Asp Ile Tyr Ser Phe Ala Ile Thr Leu Trp Gln Met
            260                 265                 270

Thr Thr Lys Gln Ala Pro Tyr Ser Gly Glu Arg Gln His Ile Leu Tyr
        275                 280                 285

Ala Val Val Ala Tyr Asp Leu Arg Pro Ser Leu Ser Ala Ala Val Phe
            290                 295                 300

Glu Asp Ser Leu Pro Gly Gln Arg Leu Gly Asp Val Ile Gln Arg Cys
305                 310                 315                 320

Trp Arg Pro Ser Ala Ala Gln Arg Pro Ser Ala Arg Leu Leu Leu Val
                325                 330                 335

Asp Leu Thr Ser Leu Lys Ala Glu Leu Gly
            340                 345

<210> SEQ ID NO 7
<211> LENGTH: 16
<212> TYPE: PRT
<213> ORGANISM: Karposi virus

<400> SEQUENCE: 7

Ala Ala Val Ala Leu Leu Pro Ala Val Leu Leu Ala Leu Leu Ala Pro
                5                   10                  15

<210> SEQ ID NO 8
<211> LENGTH: 12
<212> TYPE: PRT
<213> ORGANISM: Mammalian

<400> SEQUENCE: 8

Ala Ala Val Leu Leu Pro Val Leu Leu Ala Ala Pro
                5                   10

<210> SEQ ID NO 9
<211> LENGTH: 15
<212> TYPE: PRT
<213> ORGANISM: Mammalian

<400> SEQUENCE: 9

Val Thr Val Leu Ala Leu Gly Ala Leu Ala Gly Val Gly Val Gly
                5                   10                  15

<210> SEQ ID NO 10
<211> LENGTH: 17
<212> TYPE: PRT
<213> ORGANISM: HIV-1

<400> SEQUENCE: 10

Gly Ala Leu Phe Leu Gly Phe Leu Gly Ala Ala Gly Ser Thr Met Gly
                5                   10                  15

Ala
17
```

```
<210> SEQ ID NO 11
<211> LENGTH: 33
<212> TYPE: PRT
<213> ORGANISM: Caiman sp.

<400> SEQUENCE: 11

Met Gly Leu Gly Leu His Leu Leu Val Leu Ala Ala Ala Leu Gln Gly
                 5                  10                  15

Ala Met Gly Leu Gly Leu His Leu Leu Leu Ala Ala Ala Leu Gln Gly
            20                  25                  30

Ala
33

<210> SEQ ID NO 12
<211> LENGTH: 30
<212> TYPE: PRT
<213> ORGANISM: Influenza

<400> SEQUENCE: 12

Trp Glu Ala Lys Leu Ala Lys Ala Leu Ala Lys Ala Leu Ala Lys His
                 5                  10                  15

Leu Ala Lys Ala Leu Ala Lys Ala Leu Lys Ala Cys Glu Ala
            20                  25                  30

<210> SEQ ID NO 13
<211> LENGTH: 30
<212> TYPE: PRT
<213> ORGANISM: Influenza

<400> SEQUENCE: 13

Trp Glu Ala Ala Leu Ala Glu Ala Leu Ala Glu Ala Leu Ala Glu His
                 5                  10                  15

Leu Ala Glu Ala Leu Ala Glu Ala Leu Glu Ala Leu Glu Ala
            20                  25                  30

<210> SEQ ID NO 14
<211> LENGTH: 24
<212> TYPE: PRT
<213> ORGANISM: Artificial Sequence
<220> FEATURE:
<223> OTHER INFORMATION: Synthetic amino acid polymer

<400> SEQUENCE: 14

Leu Ala Arg Leu Leu Ala Arg Leu Leu Ala Arg Leu Leu Ala Arg Leu
                 5                  10                  15

Leu Ala Arg Leu Leu Ala Arg Leu
            20

<210> SEQ ID NO 15
<211> LENGTH: 18
<212> TYPE: PRT
<213> ORGANISM: Unknown
<220> FEATURE:
<223> OTHER INFORMATION: amphipathic cationic amino acid polymer

<400> SEQUENCE: 15

Lys Leu Leu Lys Leu Leu Leu Lys Leu Trp Lys Leu Leu Leu Lys Leu
                 5                  10                  15

Leu Lys
    18

<210> SEQ ID NO 16
<211> LENGTH: 15
```

-continued

```
<212> TYPE: PRT
<213> ORGANISM: Drosophila melanogaster

<400> SEQUENCE: 16

Arg Gln Ile Lys Ile Trp Phe Gln Arg Arg Met Lys Lys Trp Lys
                 5                  10                  15

<210> SEQ ID NO 17
<211> LENGTH: 11
<212> TYPE: PRT
<213> ORGANISM: HIV-1

<400> SEQUENCE: 17

Tyr Gly Arg Lys Lys Arg Arg Gln Arg Arg
                 5                  10

<210> SEQ ID NO 18
<211> LENGTH: 8
<212> TYPE: PRT
<213> ORGANISM: HIV-1

<400> SEQUENCE: 18

Gly Arg Lys Lys Arg Arg Gln Arg
                 5

<210> SEQ ID NO 19
<211> LENGTH: 34
<212> TYPE: PRT
<213> ORGANISM: Mammal

<400> SEQUENCE: 19

Asp Ala Ala Thr Ala Thr Arg Gly Arg Ser Ala Ala Ser Arg Pro Thr
                 5                  10                  15

Glu Arg Pro Arg Ala Pro Ala Arg Ser Ala Ser Arg Pro Arg Arg Pro
             20                  25                  30

Val Glu
     34

<210> SEQ ID NO 20
<211> LENGTH: 27
<212> TYPE: PRT
<213> ORGANISM: Artificial sequence
<220> FEATURE:
<223> OTHER INFORMATION: Composite peptide containing elements of
      galanin and mastoparan

<400> SEQUENCE: 20

Gly Trp Thr Leu Asn Ser Ala Gly Tyr Leu Leu Gly Lys Ile Asn Leu
                 5                  10                  15

Lys Ala Leu Ala Ala Leu Ala Lys Lys Ile Leu
             20                  25

<210> SEQ ID NO 21
<211> LENGTH: 1375
<212> TYPE: DNA
<213> ORGANISM: Homo sapiens

<400> SEQUENCE: 21
gaattcgcca ggaagaagcg gaggcaacga atcctggaa caaggctaca gcgtcgaaga       60
tccccagcgc tgcgggctcg gagagcagtc ctaacggcgc ctcgtacgct agtgtcctcc     120
cttttcagtc cgcgtccctc cctgggccgg gctggcactc ttgccttccc cgtccctcat    180
ggcgctgctc cgacgcccga cggtgtccag tgatttggag aatattgaca caggagttaa    240
```

-continued

```
ttctaaagtt aagagtcatg tgactattag gcgaactgtt ttagaagaaa ttggaaatag      300
agttacaacc agagcagcac aagtagctaa gaaagctcag aacaccaaag ttccagttca      360
acccaccaaa acaacaaatg tcaacaaaca actgaaacct actgcttctg tcaaaccagt      420
acagatggaa aagttggctc caaagggtcc ttctcccaca cctgaggatg tctccatgaa      480
ggaagagaat ctctgccaag cttttctga tgccttgctc tgcaaaatcg aggacattga      540
taacgaagat tgggagaacc ctcagctctg cagtgactac gttaaggata tctatcagta      600
tctcaggcag ctggaggttt tgcagtccat aaacccacat ttcttagatg gaagagatat      660
aaatggacgc atgcgtgcca tcctagtgga ttggctggta caagtccact ccaagtttag      720
gcttctgcag gagactctgt acatgtgcgt tggcattatg gatcgatttt tacaggttca      780
gccagtttcc cggaagaagc ttcaattagt tgggattact gctctgctct tggcttccaa      840
gtatgaggga atgttttctc caaatattga agactttgtt tacatcacag acaatgctta      900
taccagttcc caaatccgag aaatggaaac tctaattttg aaagaattga atttgagtt       960
gggtcgaccc ttgccactac acttcttaag gcgagcatca aaagccgggg aggttgatgt     1020
tgaacagcac actttagcca agtatttgat ggagctgact ctcatcgact atgatatggt     1080
gcattatcat ccttctaagg tagcagcagc tgcttcctgc ttgtctcaga aggttctagg     1140
acaaggaaaa tggaacttaa agcagcagta ttacacagga tacacagaga atgaagtatt     1200
ggaagtcatg cagcacatgg ccaagaatgt ggtgaaagta aatgaaaact taactaaatt     1260
catcgccatc aagaataagt atgcaagcag caaactcctg aagatcagca tgatccctca     1320
gctgaactca aaagccgtca aagaccttgc ctccccactg ataggaaggt cctag          1375
```

<210> SEQ ID NO 22
<211> LENGTH: 408
<212> TYPE: PRT
<213> ORGANISM: Homo sapiens

<400> SEQUENCE: 22

```
glu phe gly arg lys lys arg arg gln arg Met Ala Leu Leu Arg Arg
              5                  10                  15

Pro Thr Val Ser Ser Asp Leu Glu Asn Ile Asp Thr Gly Val Asn Ser
         20                  25                  30

Lys Val Lys Ser His Val Thr Ile Arg Arg Thr Val Leu Glu Glu Ile
     35                  40                  45

Gly Asn Arg Val Thr Thr Arg Ala Ala Gln Val Ala Lys Lys Ala Gln
 50                  55                  60

Asn Thr Lys Val Pro Val Gln Pro Thr Lys Thr Thr Asn Val Asn Lys
65                  70                  75                  80

Gln Leu Lys Pro Thr Ala Ser Val Lys Pro Val Gln Met Glu Lys Leu
                 85                  90                  95

Ala Pro Lys Gly Pro Ser Pro Thr Pro Glu Asp Val Ser Met Lys Glu
            100                 105                 110

Glu Asn Leu Cys Gln Ala Phe Ser Asp Ala Leu Leu Cys Lys Ile Glu
        115                 120                 125

Asp Ile Asp Asn Glu Asp Trp Glu Asn Pro Gln Leu Cys Ser Asp Tyr
    130                 135                 140

Val Lys Asp Ile Tyr Gln Tyr Leu Arg Gln Leu Glu Val Leu Gln Ser
145                 150                 155                 160

Ile Asn Pro His Phe Leu Asp Gly Arg Asp Ile Asn Gly Arg Met Arg
                165                 170                 175
```

```
Ala Ile Leu Val Asp Trp Leu Val Gln Val His Ser Lys Phe Arg Leu
            180                 185                 190

Leu Gln Glu Thr Leu Tyr Met Cys Val Gly Ile Met Asp Arg Phe Leu
        195                 200                 205

Gln Val Gln Pro Val Ser Arg Lys Lys Leu Gln Leu Val Gly Ile Thr
    210                 215                 220

Ala Leu Leu Leu Ala Ser Lys Tyr Glu Glu Met Phe Ser Pro Asn Ile
225                 230                 235                 240

Glu Asp Phe Val Tyr Ile Thr Asp Asn Ala Tyr Thr Ser Ser Gln Ile
                245                 250                 255

Arg Glu Met Glu Thr Leu Ile Leu Lys Glu Leu Lys Phe Glu Leu Gly
            260                 265                 270

Arg Pro Leu Pro Leu His Phe Leu Arg Arg Ala Ser Lys Ala Gly Glu
        275                 280                 285

Val Asp Val Glu Gln His Thr Leu Ala lys Tyr Leu Met Glu Leu thr
    290                 295                 300

Leu Ile Asp Tyr Asp Met Val His Tyr His Pro Ser Lys Val Ala Ala
305                 310                 315                 320

Ala Ala Ser Cys Leu Ser Gln Lys Val Leu Gly Gln Gly Lys Trp Asn
                325                 330                 335

Leu Lys Gln Gln Tyr Tyr Thr Gly Tyr Thr Glu Asn Glu val Leu Glu
            340                 345                 350

Val Met Gln His Met Ala Lys Asn Val Val Lys Val Asn Glu Asn Leu
        355                 360                 365

Thr Lys Phe Ile Ala Ile Lys Asn Lys Tyr Ala Ser Ser Lys Leu Leu
    370                 375                 380

Lys Ile Ser Met Ile Pro Gln Leu Asn Ser Lys Ala Val Lys Asp Leu
385                 390                 395                 400

Ala Ser Pro Leu Ile Gly Arg Ser
                405

<210> SEQ ID NO 23
<211> LENGTH: 55
<212> TYPE: DNA
<213> ORGANISM: Artificial sequence
<220> FEATURE:
<223> OTHER INFORMATION: Synthetic single-stranded oligonucleotide
                        primer

<400> SEQUENCE: 23
aaaagaattc ggcaggaaga agcggaggca acgaatggcg ctcagggtca ctagg        55

<210> SEQ ID NO 24
<211> LENGTH: 34
<212> TYPE: DNA
<213> ORGANISM: Artificial sequence
<220> FEATURE:
<223> OTHER INFORMATION: Synthetic single-stranded oligonucleotide
                        primer

<400> SEQUENCE: 24
ttttgcggcc gctgcctttg tcacggcctt agac                              34

<210> SEQ ID NO 25
<211> LENGTH: 1336
<212> TYPE: DNA
<213> ORGANISM: Mus musculus

<400> SEQUENCE: 25
```

```
aaaagaattc ggcaggaaga agcggaggca acgaatggcg ctcagggtca ctaggaacac       60
gaaaattaac gcagaaaata aggccaaggt cagtatggca ggcgccaagc gtgtgcctgt      120
gacagttact gctgcttcca agcccgggct gagaccgaga actgctcttg gagacattgg      180
taataaagtc agcgaagagc tacaggcaac agtgcctctg aaaagggaag caaaaacgct      240
aggtactgga aaaggtactg ttaaagcccc accaaaacct gtagagaagg tgcctgtgtg      300
tgaaccagag gtggaacttg ctgaacctga gcctgaacct gaacttgaac atgttagaga      360
agagaagctt tctcctgaac ctattttggt tgataatccc tctccaagcc cgatggaaac      420
atgtggatgt gcgcctgcag aagagtatcc gtgtcaggct ttctctgatg taatccttgc      480
agtgagtgac gtagacgcag atagtggggc tgacccaaac ctctgtagtg aatatgtgaa      540
agatatctat gcttatctcc gacaactgga ggaagagcag tcagttagac caaaatacct      600
acagggtcgt gaagtgactg gaaacatgag agctatcctc attgactggc taatacaggt      660
tcagatgaaa tttaggctgc ttcaggagac catgtacatg actgtgtcca ttattgatcg      720
gttcatgcag aacagttgtg tgcccaagaa gatgatacag ctggtcggtg taacggccat      780
gtttattgca agcaaatatg aagacatgta cccaccagaa ataggtgact cgcctttgt       840 gactaacaac acgtacacta agcaccagat cagacagatg gagatgaaga ttctcagagt      900
tctgaacttc agcctgggtc gccctctgcc tctgcacttc ctccgtagag catctaaagt      960
cggagaggtt gacgtcaggc agcacactct ggccaaatac ctcatggagc tctccatgct     1020
ggactacgac atggtgcatt ttgctccttc cagggcattt tctggggctt tctgcttagc     1080
gctggaaatt cttgacaacg gtgaatggac accaactctg cagcactacc tatcctacag     1140
tgaagactcc ctgcttcctg ttatgcagca cctggctaag aatgtagtca tggtgaactg     1200
tggcctcaca aagcacatga ctgtcaagaa caagtatgca gcatctaagc atgctaagat     1260
cagcacgctg gcacagctga actgtacaca tgttcagaat ttgtctaagg ccgtgacaaa     1320
ggcagcggcc gcaaaa                                                    1336
```